US009302030B2

(12) United States Patent
Hossainy et al.

(10) Patent No.: US 9,302,030 B2
(45) Date of Patent: Apr. 5, 2016

(54) PROHEALING PIEZOELECTRIC COATINGS

(71) Applicant: Abbott Cardiovascular Systems Inc., Santa Clara, CA (US)

(72) Inventors: Syed Faiyaz Ahmed Hossainy, Hayward, CA (US); Mikael Trollsas, San Jose, CA (US); Lothar Walter Kleiner, Los Altos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/476,597

(22) Filed: Sep. 3, 2014

(65) Prior Publication Data

US 2014/0370072 A1 Dec. 18, 2014

Related U.S. Application Data

(62) Division of application No. 11/890,904, filed on Aug. 7, 2007, now abandoned.

(51) Int. Cl.

| | |
|---|---|
| ***A61L 31/10*** | (2006.01) |
| ***A61L 31/16*** | (2006.01) |
| ***C08F 114/28*** | (2006.01) |
| ***C08F 214/28*** | (2006.01) |
| ***C08F 114/22*** | (2006.01) |
| ***C08F 214/22*** | (2006.01) |

(52) U.S. Cl.

CPC ................. *A61L 31/10* (2013.01); *A61L 31/16* (2013.01); *C08F 114/22* (2013.01); *C08F 214/22* (2013.01); *C08F 214/28* (2013.01); *A61L 2300/416* (2013.01); *A61L 2420/04* (2013.01)

(58) Field of Classification Search

None

See application file for complete search history.

(56) References Cited

U.S. PATENT DOCUMENTS

| | | | | |
|---|---|---|---|---|
| 6,777,214 | B1 * | 8/2004 | Yamashita | A61L 24/001 423/299 |
| 2002/0127391 | A1 * | 9/2002 | Kumar | A61L 27/28 428/325 |
| 2007/0040478 | A1 * | 2/2007 | Tofail | A61L 27/32 310/328 |

* cited by examiner

*Primary Examiner* — Robert A Wax
*Assistant Examiner* — Caralynne Helm
(74) *Attorney, Agent, or Firm* — Squire Patton Boggs (US) LLP

(57) ABSTRACT

Provided herein is a prohealing piezoelectric coating and the method of making and using the same.

6 Claims, No Drawings

PROHEALING PIEZOELECTRIC COATINGS

CROSS-REFERENCE TO RELATED APPLICATION

This application is a divisional application of U.S. application Ser. No. 11/890,904 filed on Aug. 7, 2007, which is incorporated by reference as if fully set forth, including any drawings, herein.

BACKGROUND

1. Field of the Invention

This invention is generally related to coatings for implantable medical devices, such as drug delivery vascular stents.

2. Description of the State of the Art

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical bypass operation. To reduce the partial or total occlusion of the artery by the collapse of the arterial lining and to reduce the chance of thrombosis or restenosis, a stent is implanted in the artery to keep the artery open.

Drug delivery stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, ISR still poses a significant problem given the large volume of coronary interventions and their expanding use. The pathophysiological mechanism of ISR involves interactions between the cellular and acellular elements of the vessel wall and the blood. Damage to the endothelium during PCI constitutes a major factor for the development of ISR (see, e.g., Kipshidze, N., et al., J. Am. Coll. Cardiol. 44:733-739 (2004)).

The embodiments of the present invention address these concerns as well as others that are apparent to one having ordinary skill in the art.

SUMMARY

Provided herein is a piezoelectric coating and the method of making the same. The piezoelectric coating includes a piezoelectric polymer or material. The piezoelectricity of the coating provides enhanced endothelization of the coating and imparts to the coating enhanced prohealing properties.

In some embodiments, the piezoelectric coating can include a piezoelectric polymer. The piezoelectric polymer can be any polymers that are piezoelectric.

As used herein, the term piezoelectric or piezoelectricity refers to the attributes of a polymer to generate a charge in response to applied mechanical stress. If the material is not short-circuited, the applied charge induces a voltage across the material.

In some embodiments, the piezoelectric polymer is a poled fluoropolymer. The fluoropolymer can be any polymer that includes fluoro grouping or atoms. In some embodiments, the fluoropolymer is poly(vinylidene fluoride) (PVDF), poly(vinylidene fluoride-co-hexafluoropropylene) (PVDF-HFP), poly(vinylidene fluoride-co-trifluoroethylene) (PVDF-TrFE), poly(vinylidene fluoride-co-tetrafluoroethylene) (PVDF-TFE), other co-polymers based on PVDF or polymers which can have piezoelectric properties, or combinations thereof.

In some embodiments, the prohealing piezoelectric coating can include a chemo-attractant for endothelial cells. Release of the chemo-attractant can recruit endothelial cells to the coating. In some embodiments, the coating can include one or more polymers that are capable of controlling the chemo-attractant's release. The chemo-attractant can diffuse through the polymer coating, through a layer of absorbed proteins and cells (acute phase after implantation), and through the neo-intima (long-term phase) to the lumen surface in an amount sufficient to recruit endothelial cells or endothelial progenitor cells to the surface.

In some embodiments, the piezoelectric coating can include a bioactive agent other than the chemo-attractant for endothelial cells described above. Any bioactive agent can be included in a coating with the chemo-attractant described herein. Some examples of the bioactive agent include siRNA and/or other oligoneucleotides that inhibit endothelial cell migration. The bioactive agent can also be lysophosphatidic acid (LPA) or sphingosine-1-phosphate (SIP). LPA is a "bioactive" phospholipid able to generate growth factor-like activities in a wide variety of normal and malignant cell types. LPA plays an important role in normal physiological processes such as wound healing, and in vascular tone, vascular integrity, or reproduction. Some other exemplary bioactive agents are paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, prodrugs thereof, co-drugs thereof, and combinations thereof.

The coating can be formed on an implantable device such as a stent, which can be implanted in a patient to treat, prevent, mitigate, or reduce a vascular medical condition, or to provide a pro-healing effect. Examples of these conditions include atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

Provided herein is a piezoelectric coating and the method of making the same. The piezoelectric coating includes a piezoelectric polymer or material. The piezoelectricity of the coating provides enhanced endothelization of the coating and imparts to the coating enhanced prohealing properties.

In some embodiments, the piezoelectric coating can include a piezoelectric polymer. The piezoelectric polymer can be any polymers that are piezoelectric.

As used herein, the term piezoelectric or piezoelectricity refers to the attributes of a polymer to generate a charge in response to applied mechanical stress. If the material is not short-circuited, the applied charge induces a voltage across the material.

In some embodiments, the piezoelectric polymer is a poled fluoropolymer. The fluoropolymer can be any polymer that includes fluoro grouping or atoms. In some embodiments, the fluoropolymer is poly(vinylidene fluoride) (PVDF), poly(vinylidene fluoride-co-hexafluoropropylene) (PVDF-HFP), poly(vinylidene fluoride-co-trifluoroethylene) (PVDF-TrFE), poly(vinylidene fluoride-co-tetrafluoroethylene) (PVDF-TFE), other co-polymers based on PVDF or polymers which can have piezoelectric properties, or combinations thereof. In some embodiments, a fluoropolymer is a polymer of any polymer including units derived from fluoro vinyl monomers.

The term “poled” refers to the molecules of a polymer being oriented toward a direction.

In some embodiments, the prohealing piezoelectric coating can include a chemo-attractant for endothelial cells. Release of the chemo-attractant can recruit endothelial cells to the coating. In some embodiments, the coating can include one or more polymers that are capable of controlling the chemo-attractant's release. The chemo-attractant can diffuse through the polymer coating, through a layer of absorbed proteins and cells (acute phase after implantation), and through the neo-intima (long-term phase) to the lumen surface in an amount sufficient to recruit endothelial cells or endothelial progenitor cells to the surface.

In some embodiments, the piezoelectric coating can include a bioactive agent other than the chemo-attractant for endothelial cells described above. Any bioactive agent can be included in a coating with the chemo-attractant described herein. Some examples of the bioactive agent include siRNA and/or other oligoneucleotides that inhibit endothelial cell migration. The bioactive agent can also be lysophosphatidic acid (LPA) or sphingosine-1-phosphate (SIP). LPA is a “bioactive” phospholipid able to generate growth factor-like activities in a wide variety of normal and malignant cell types. LPA plays an important role in normal physiological processes such as wound healing, and in vascular tone, vascular integrity, or reproduction. Some other exemplary bioactive agents are paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, prodrugs thereof, co-drugs thereof, and combinations thereof.

The coating can be formed on an implantable device such as a stent, which can be implanted in a patient to treat, prevent, mitigate, or reduce a vascular medical condition, or to provide a pro-healing effect. Examples of these conditions include atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

Piezoelectric Coating

The piezoelectric coating described herein can include any piezoelectric polymer or material. In some embodiments, the coating can include a piezoelectric polymer. In some embodiments, the coating can include a piezoelectric material that is not a polymer, such as a piezoelectric ceramic, or a piezoelectric polymer-ceramic composite.

Piezoelectric Polymer

The piezoelectric polymer that can be included in a piezoelectric coating described herein can be any piezoelectric polymer. In some embodiments, the piezoelectric polymer is a fluoropolymer. Some examples of fluoropolymers include Solef™ polymers. One example of Solef™ polymers is PVDF. In some embodiments, the piezoelectric polymer is a copolymer comprising PVDF-HFP.

Polyvinylidene Fluoride (PVDF)—

PVDF exhibits piezoelectricity several times larger than quartz. Unlike ceramics, where the crystal structure of the material creates the piezoelectric effect, in polymers the intertwined long-chain molecules attract each and repel other when an external force is applied. The desired morphology of PVDF is known as the β phase or Form I, in which the predominantly “head to tail” polymer chains have an all-trans extended planar zig-zag form with the dipoles of adjacent chains parallel to one another. This β phase can be formed from the more common alpha phase (Form II), which is nonpolar, by mechanical deformation followed by electrical polarization. In practice, both uniaxial and biaxial mechanical orientation is used which, after poling, gives a different balance of piezo/pyro-electric properties.

The process of transforming a piezoelectric material from the nonpolar alpha phase to the dipolar β phase is well known in the art. An exemplary process is described in U.S. Pat. No. 4,427,609.

Other piezoelectric polymers include, but are not limited to, polyvinylidene fluoride (PVDF) and copolymers films of PVDF, which possess the highest values of piezoelectric constants of any known polymer.

In some embodiments, the piezoelectric coating can specifically exclude any of the above listed piezoelectric polymer or polymers.

Piezoelectric Material

The piezoelectric material other than the piezoelectric polymer described above that can be included in a piezoelectric coating can be any piezoelectric material. In some embodiments, the piezoelectric material is a piezoelectric ceramic compound. Some examples of the piezoelectric material include, but are not limited to, lead zirconium titanate (PZT), lead scandium tantalate, barium strontium titanate, lead magnesium niobate, or combinations thereof. Some further examples of piezoelectric materials include, but are not limited to, $Pb(xZr,(1-x)Ti)O_3$, $BaTiO_3$, $PbZrO_3$, $PbTiO_3$, $PbNb_2O_6$, $(Pb,Ca)TiO_3$, $(Pb,Sm)TiO_3$, $Pb(NbO_2)_2/PbTiO_3$, $(1-x)Pb(Mg_{1/3}\ Nb_{2/3})O_3\text{-}xPbTiO_3$, $(1-x-y)Pb(Zn_{1/3}Nb_{2/3})O_3\text{-}xPbTiO_3\text{-}yBaTiO_3$, and $(1-x-y)Pb(Zn_{1/3}Nb_{2/3})O_3\text{-}xBaTiO_3\text{-}yPbTiO_3$, xPZN-(1−x)PMN, xPMN-(1−x)PZT, PNN-PZ-PT, xPZN-(1−x)PZT, or combinations thereof.

Other piezoelectric materials that can be included in a piezoelectric coating include, but are not limited to, polymer-ceramic composites, which can be a blend or multi-layer composites. Generally, a polymer-ceramic composite includes a piezoelectric phase and a non-piezoelectric phase. The piezoelectric phase includes at least one piezoelectric material, and the non-piezoelectric phase includes a binder material which can be, e.g., a polymer. An example of such a multi-layer composite contains a PVDF and a piezoelectric ceramic. Some other examples of such polymer-ceramic composites or multi-layer composites are described in U.S. Pat. Nos. 5,505,870; and 5,796,207, the teachings of which are incorporated herein in its entirety by reference.

In some embodiments, the piezoelectric coating can specifically exclude any of the above listed piezoelectric material or materials.

Polarization

The piezoelectric coating described herein can be formed onto an implantable device (e.g., a stent) and then subjected to high electric voltage. The high electric voltage can pole the piezoelectric polymer or material to orient the polymer(s) or material(s), resulting in polarization of the piezoelectric polymer(s) or material(s).

Generally, the piezoelectric coating receiving a high electric voltage treatment will be in a condition that is capable of allowing the piezoelectric polymer(s) or material to re-orient or to polarize. Such condition can include, e.g., solvated or wetted condition. In some embodiments, such condition can be, e.g., heating the coating to a temperature at or above glass transition temperature ($T_g$) of the coating.

Polarization of the piezoelectric polymer(s) or material(s) in the coating can be fixed or frozen in the coating by causing the coating to solidify from a less solidified condition by, e.g., evaporation of solvent in the coating or cooling the coating from a temperature above, e.g., $T_g$ of the coating to a temperature below $T_g$ of the coating. Following implant of an implantable device comprising the piezoelectric coating, the cyclic motion of the vessel will induce faster healing for that the coronary artery behaves like a peristaltic pump, oscillations in charge are induced due to pulsatile flow. This pulsatile flow promotes vascular healing.

As used herein, the term high voltage refers to a direct current (DC) having a voltage at about (e.g., 100 V) or above. The term low voltage refers to a DC current having a voltage at about 10V or below, e.g. 3V.

Some examples of treating the piezoelectric coating by a high electric voltage are described below:

a) A piezoelectric coating comprising a piezoelectric polymer or material can be subjected to high electric voltage before the coating is dried (e.g., in a convection oven). The high electric voltage can pole and orient the piezoelectric polymer or material and cause the polarization to fix when the coating is dried. For example, a coating comprising PVDF can be subjected to the treatment of a high electric voltage in this fashion.

b) A piezoelectric coating formed on an implantable device comprising a piezoelectric polymer(s) or material(s) can be exposed to a solvent vapor (e.g., acetone vapor) and simultaneously or subsequently subjected to the treatment of a high electric voltage to re-orient to generate polarization of the piezoelectric polymer(s) or material(s). Removal of the solvent vapor and dry the coating, which may take in some solvent as the result of exposure to the solvent vapor, can cause the piezoelectric polymer(s) or material(s) to fix the polarization. The solvent for forming the solvent vapor is chosen on the condition that such solvent can solvate or wet the piezoelectric coating subjected to the treatment of high electric voltage. A person of ordinary skill in the art can readily chosen a solvent to form a solvent vapor based on the chemical nature of the piezoelectric coating. For example, for a piezoelectric coating comprising PVDF, acetone or any other solvent that can solvate or wet PVDF can be used to form the solvent vapor.

c) Immediately after each coating pass, a high voltage pulse can be delivered to a piezoelectric coating thus formed comprising a piezoelectric polymer(s) or material(s). The pulses are so synchronized so that the polarization relaxation time of the piezoelectric polymer(s) or material(s) exceeds the drying time so that the polarization is fixed or frozen in the coating. Generally, the high voltage pulses can have a voltage as described above and a duration of approximately ten second or less, about one second or less, or about 0.1 second or less. The pulses can be synchronized, and a person of ordinary skill in the art can readily appreciate the ways to synchronize the pulses to cause the polarization relaxation time of the piezoelectric polymer(s) or material(s) to exceed the drying time so that the polarization is fixed or frozen in the coating.

d) During coating a composition comprising a piezoelectric polymer(s) or material(s) onto an implantable device, a high voltage pulse can be delivered to the coating. The pulses are so synchronized so that the polarization relaxation time of the piezoelectric polymer(s) or material(s) exceeds the drying time so that the polarization is fixed or frozen in the coating. Generally, the high voltage pulses can have a voltage as described above and a duration of approximately ten second or less, about one second or less, or about 0.1 second or less. The pulses can be synchronized, and a person of ordinary skill in the art can readily appreciate the ways to synchronize the pulses to cause the polarization relaxation time of the piezoelectric polymer(s) or material(s) to exceed the drying time so that the polarization is fixed or frozen in the coating.

The methods of coating an implantable device are well documented in the art. Generally, the method includes (a) providing a coating composition and (b) applying the coating composition onto an implantable medical device to form a coating on the implantable medical device. The coating composition can include any polymer(s), material(s), bioactive agent(s) for forming the piezoelectric coating described herein.

Biocompatible Polymers

The piezoelectric coating described herein can include one or more biocompatible polymer other than the piezoelectric polymer(s) or material(s) described above. The biocompatible polymer can be biodegradable (both bioerodable or bioabsorbable) or nondegradable and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly (isobutyl methacrylate), poly(tert-butyl methacrylate), poly (n-propyl methacrylate), poly(isopropyl methacrylate), poly (ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly (ether ester), polyalkylene oxalates, polyphosphazenes, phosphoryl choline, choline, poly(aspirin), polymers and copolymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), PLURONIC™ surfactants (polypropylene oxide-co-polyethylene glycol), poly(tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof. In some embodiments, the copolymer described herein can exclude any one or more of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

Biologically Active Agents

The implantable device described herein can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammmatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.,* 70A:10-19 (2004). Endothelial cells can be selectively targeted (for the targeted delivery of immunoliposomes) using scFv A5. T. Volkel, et al., *Biochimica et Biophysica Acta,* 1663:158-166 (2004). Junction membrane protein vascular endothelial (VE)-cadherin has been shown to bind to endothelial cells and down regulate apoptosis of the endothelial cells. R. Spagnuolo, et al., *Blood,* 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is clobetasol.

In some embodiments, optionally in combination with one or more other embodiments described herein, the at least one biologically active agent specifically cannot be one or more of any of the bioactive drugs or agents described herein.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Implantable Device

As used herein, an implantable device can be any suitable medical substrate that can be implanted in a human or veterinary patient. Examples of such implantable devices include self-expandable stents, balloon-expandable stents, stent-grafts, grafts (e.g., aortic grafts), heart valve prosthesis (e.g., artificial heart valves) or vascular graft, cerebrospinal fluid shunts, pacemaker electrodes, catheters, endocardial leads (e.g., FINELINE and ENDOTAK, available from Guidant Corporation, Santa Clara, Calif.), and devices facilitating anastomosis such as anastomotic connectors. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device can be, for example, a bioabsorbable stent.

Method of Use

In accordance with embodiments of the invention, a chemo-attractant can be included in an implantable device or prosthesis, e.g., a stent. For a device including one or more active agents, the agent will retain on the device such as a stent during delivery and expansion of the device, and released at a desired rate and for a predetermined duration of time at the site of implantation.

Preferably, the device is a stent. The stent described herein is useful for a variety of medical procedures, including, by way of example, treatment of obstructions caused by tumors in the bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of generating piezoelectric polarization in a coating on an implantable device, comprising:

forming the coating comprising a piezoelectric material(s) onto the implantable device, providing acetone vapor to the coating, subjecting the coating to high electric voltage to generate polarization of the piezoelectric material(s), and removing the acetone vapor from the coating and causing the coating to dry, thereby fixing the polarization of the piezoelectric material(s) in the coating.

2. The method of claim 1, wherein the piezoelectric material comprises a piezoelectric ceramic or a polymer-ceramic composite.

3. The method of claim 2, wherein the polymer-ceramic composite comprises a multi-layer composite containing a polymer and a ceramic.

4. The method of claim 2, wherein the piezoelectric ceramic is selected from PZT, lead scandium tantalate, barium strontium titanate, lead magnesium niobate, or combinations thereof.

5. The method of claim 2, wherein the piezoelectric ceramic is selected from $Pb(xZr,(1-x)Ti)O_3$, $BaTiO_3$, $PbZrO_3$, $PbTiO_3$, $PbNb_2O_6$, $(Pb,Ca)TiO_3$, $(Pb,Sm)TiO_3$, $Pb(NbO_2)_2/PbTiO_3$, $(1-x)Pb(Mg_{1/3}Nb_{2/3})O_3$-$xPbTiO_3$, $(1-x-y)Pb(Zn_{1/3}Nb_{2/3})O_3$-$xPbTiO_3$-$yBaTiO_3$, and $(1-x-y)Pb(Zn_{1/3}Nb_{2/3})O_3$-$xBaTiO_3$-$yPbTiO_3$, xPZN-(1−x)PMN, xPMN-(1−x)PZT, PNN-PZ-PT, xPZN-(1−x)PZT, or combinations thereof.

6. The method of claim 1, wherein the coating further comprises at least one bioactive agent.

* * * * *